United States Patent
Tahara (10) Patent No.: US 10,942,108 B2
(45) Date of Patent: Mar. 9, 2021

(54) FINE PARTICLE MEASUREMENT APPARATUS, INFORMATION PROCESSING APPARATUS, AND INFORMATION PROCESSING METHOD

(71) Applicant: SONY CORPORATION, Tokyo (JP)

(72) Inventor: Katsutoshi Tahara, Tokyo (JP)

(73) Assignee: SONY CORPORATION, Tokyo (JP)

( * ) Notice: Subject to any disclaimer, the term of this patent is extended or adjusted under 35 U.S.C. 154(b) by 160 days.

(21) Appl. No.: 16/067,403

(22) PCT Filed: Oct. 17, 2016

(86) PCT No.: PCT/JP2016/080653
§ 371 (c)(1),
(2) Date: Jun. 29, 2018

(87) PCT Pub. No.: WO2017/126170
PCT Pub. Date: Jul. 27, 2017

(65) Prior Publication Data
US 2019/0011348 A1    Jan. 10, 2019

(30) Foreign Application Priority Data

Jan. 22, 2016  (JP) ................. 2016-010506
Aug. 19, 2016  (JP) ................. 2016-161025

(51) Int. Cl.
G01N 15/10   (2006.01)
G01N 15/14   (2006.01)
G01N 21/64   (2006.01)
C12M 1/34    (2006.01)

(52) U.S. Cl.
CPC .......... *G01N 15/1012* (2013.01); *C12M 1/34* (2013.01); *G01N 15/1429* (2013.01);
(Continued)

(58) Field of Classification Search
CPC .......... G01N 15/1012; G01N 15/1429; G01N 15/1459; G01N 21/64; G01N 21/6428; C12M 1/34
See application file for complete search history.

(56) References Cited

U.S. PATENT DOCUMENTS

2004/0119974 A1*  6/2004  Bishop ............... G01N 15/1459
                                              356/317
2005/0073686 A1*  4/2005  Roth .................. G01N 15/1404
                                              356/436
(Continued)

FOREIGN PATENT DOCUMENTS

CN    101460827 A    6/2009
EP    1431745 A1     6/2004
(Continued)

OTHER PUBLICATIONS

International Search Report and Written Opinion of PCT Application No. PCT/JP2016/080653, dated Nov. 29, 2016, 08 pages of ISRWO.

*Primary Examiner* — David P Porta
*Assistant Examiner* — Jeremy S Valentiner
(74) *Attorney, Agent, or Firm* — Chip Law Group (57) ABSTRACT

To provide a technology that an output level difference is corrected with high accuracy in fine particle measurement that optically measures properties of fine particles. The present technology provides a fine particle measurement apparatus including a detector that detects light from fluorescent reference particles that emit fluorescence having a predetermined wavelength bandwidth, and an information processor that specifies a relationship between an applied voltage coefficient corresponding to a feature amount of a predetermined output pulse and a control signal of the detector on the basis of a feature amount of an output pulse detected by the detector and the control signal of the detector
(Continued)

at the time of detecting the feature amount of the output pulse, the feature amount of the output pulse being dependent on the control signal of the detector, or the like.

10 Claims, 8 Drawing Sheets

(52) U.S. Cl.
CPC ......... G01N 15/1459 (2013.01); G01N 21/64 (2013.01); G01N 21/6428 (2013.01); *G01N 2015/1006* (2013.01)

(56) References Cited

U.S. PATENT DOCUMENTS

2005/0112541 A1* 5/2005 Durack ................ C12N 5/0612
　　　　　　　　　　　　　　　　　　　　　　　435/2
2010/0120059 A1　　5/2010　Yan et al.
2012/0114525 A1* 5/2012 Sakazume .............. G01N 21/76
　　　　　　　　　　　　　　　　　　　　　　　422/52
2019/0003951 A1* 1/2019 Sekimoto ........... G01N 15/1012

FOREIGN PATENT DOCUMENTS

| | | |
|---|---|---|
| EP | 1656547 A2 | 5/2006 |
| EP | 2187199 A1 | 5/2010 |
| JP | 10-311789 A | 11/1998 |
| JP | 2003-083894 A | 3/2003 |
| JP | 2004-205508 A | 7/2004 |
| JP | 2007-508526 A | 4/2007 |
| JP | 2011-085587 A | 4/2011 |
| JP | 2015-025824 A | 2/2015 |
| KR | 10-2006-0065684 A | 6/2006 |
| WO | 2005/017499 A2 | 2/2005 |

* cited by examiner

FINE PARTICLE MEASUREMENT APPARATUS, INFORMATION PROCESSING APPARATUS, AND INFORMATION PROCESSING METHOD

CROSS REFERENCE TO RELATED APPLICATIONS

This application is a U.S. National Phase of International Patent Application No. PCT/JP2016/080653 filed on Oct. 17, 2016, which claims priority benefit of Japanese Patent Application No. JP 2016-010506 filed in the Japan Patent Office on Jan. 22, 2016 and also claims priority benefit of Japanese Patent Application No. JP 2016-161025 filed in the Japan Patent Office on Aug. 19, 2016. Each of the above-referenced applications is hereby incorporated herein by reference in its entirety.

TECHNICAL FIELD

The present technology relates to a fine particle measurement apparatus that optically measures properties of fine particles and, more particularly, to a fine particle measurement apparatus that optically measures properties of fine particles such as cells, an information processing apparatus, and an information processing method.

BACKGROUND ART

In recent years, along with progress of an analysis technique, a technique is developed to flow biological fine particles such as cells and microorganisms, fine particles such as microbeads, or the like in a flow path, to individually measure the fine particles, and to analyze or dispense the measured fine particles.

Among typical techniques of analyzing or dispensing fine particles, the analysis technique, which is called as a flow cytometry, is rapidly technically improved. The flow cytometry is the technique of analyzing or dispensing fine particles by flowing fine particles to be analyzed in the state of aligning the fine particles in a fluid, irradiating the fine particles with laser light or the like, and detecting fluorescence or scattered light emitted from the respective fine particles.

For example, in a case where fluorescence from cells is detected, the cells labelled with a fluorescent dye are irradiated with excitation light such as laser light having an adequate wavelength and intensity. Then, fluorescence emitted from the fluorescent dye is collected by a lens, etc., light in an adequate wavelength region is selected by using a wavelength selection device such as a filter and a dichroic mirror, and the selected light is detected by using a light-receiving device such as a PMT (photo multiplier tube). At this time, by combining a plurality of wavelength selection devices and light-receiving devices, it is possible to concurrently detect and analyze fluorescence from a plurality of fluorescent dyes that label the cells. Further, by combining excitation lights having a plurality of wavelengths, it is possible to increase the number of fluorescent dyes that can be analyzed.

The fluorescence detection by the flow cytometry is not only by a method of selecting a plurality of lights in discontinuous wavelength regions by using a wavelength selection device such as a filter and measuring light intensities in the respective wavelength regions, but also by a method of measuring fluorescence spectra of light intensities in continuous wavelength regions. In a spectrum flow cytometry capable of measuring fluorescence spectra, fluorescence emitted from fine particles is spectrally diffracted by using a spectrum device such as a prism and a grating. Then, the spectrally diffracted fluorescence is detected by using a light-receiving device array on which a plurality of light-receiving devices having different detection wavelength regions are arrayed. Examples of the light-receiving device array include a PMT array on which light-receiving devices, i.e., PMTs, are one-dimensionally arranged, a photodiode array on which light-receiving devices, i.e., photodiodes, are one-dimensionally arranged, or an array on which detection channels such as two-dimensional light-receiving devices, e.g., CCD, CMOS, etc., are arranged.

In the analysis of fine particles exemplified by a flow cytometry, an optical technique is often used in which fine particles to be analyzed are irradiated with light such as laser and fluorescence or scattered light emitted from the fine particles is detected. On the basis of detected optical information, a histogram is extracted by using a computer and software for analysis and analysis is done.

In the optical analysis of the fine particles, a quality control (QC) may be performed to examine accuracy, confirm an operation of the device, standardize, and the like before the fine particles to be actually tested are optically measured. In the quality control, a plurality of beads labeled with fluorescent dyes generally having different fluorescence intensities (for example, 3 peak beads, 6 peak beads, 8 peak beads, and the like), one type of beads providing a wide range of spectra (for example, Align Check Beads, or Ultra Rainbow fluorescent particles) or the like is used.

In a case where the measurement is performed by using a plurality of fluorescent dyes, a fluorescence correction is performed. For example, Patent Literature 1 discloses the technology capable of performing a fluorescence correction among a plurality of fluorescent dyes or during fluorescence is measured by using a plurality of laser lights and performing the fluorescence correction without preparing samples again even after measurement processing of cells to be tested is ended, which is realized by developing a program. The program is such that correction calculation is performed on a fluorescence value by using a fluorescence value of fluorescence labeled cells to be tested corresponding to a center of gravity value and a predetermined determinant, the center of gravity value of a fluorescence group of the fluorescence labeled cells to be tested being calculated from a two-dimensional correlation diagram of the fluorescence labeled cells to be tested acquired by a flow cytometer.

CITATION LIST

Patent Literature

Patent Literature 1: Japanese Patent Application Laid-open No. 2003-83894

DISCLOSURE OF INVENTION

Technical Problem

The photodetectors such as PMTs have a sensitivity difference from one photodetector to another and may have a sensitivity difference over time even in the same photodetector. One of the causes of the sensitivity difference is a variation in sensitivities of the photodetector. The variation in sensitivities may differ several tens times or more from one photodetector to another or over time, even if a same voltage value is set. This predominantly and directly leads to an output level difference among apparatuses. Accordingly, the output level may differ even if a setting is made same as that of the former measurement among the apparatuses or within the apparatus.

Accordingly, it is an object of the present technology to provide a technology that an output level difference can be corrected with high accuracy in fine particle measurement that optically measures properties of fine particles.

Solution to Problem

As a result of intensive studies in order to solve the above-described object, the present inventors have been succeeded in correcting an output level difference with high accuracy by specifying a relationship between an applied voltage coefficient corresponding to a feature amount of a predetermined output pulse and a control signal of a detector and have completed the present technology.

Specifically, the present technology provides a fine particle measurement apparatus including a detector that detects light from fluorescent reference particles that emit fluorescence having a predetermined wavelength bandwidth, and an information processor that specifies a relationship between an applied voltage coefficient corresponding to a feature amount of a predetermined output pulse and a control signal of the detector on the basis of a feature amount of an output pulse detected by the detector and the control signal of the detector at the time of detecting the feature amount of the output pulse, the feature amount of the output pulse being dependent on the control signal of the detector.

The detector may include a plurality of PMTs. In this case, there may be an output difference among the plurality of PMTs.

The feature amount of the output pulse may be a height of the output pulse or an area of the output pulse. In particular, the feature amount of the output pulse may be a height of the output pulse.

The information processor may correct the control signal on the basis of the applied voltage coefficient. In this case, the detector to which the corrected control signal is input may measure target fine particles.

Also, the present technology provides an information processing apparatus including an information processor that specifies a relationship between an applied voltage coefficient corresponding to a feature amount of a predetermined output pulse and a control signal of the detector on the basis of a feature amount of an output pulse detected by a detector that detects light from fluorescent reference particles that emit fluorescence having a predetermined wavelength bandwidth and the control signal of the detector at the time of detecting the feature amount of the output pulse, the feature amount of the output pulse being dependent on the control signal of the detector.

The feature amount of the output pulse may be a height of the output pulse or an area of the output pulse. In particular, the feature amount of the output pulse may be a height of the output pulse.

The information processor may correct the control signal on the basis of the applied voltage coefficient.

The information processing apparatus according to the present technology may further include a memory that stores the applied voltage coefficient.

Furthermore, the present technology also provides an information processing method including an information processing step of specifying a relationship between an applied voltage coefficient corresponding to a feature amount of a predetermined output pulse and a control signal of the detector on the basis of a feature amount of an output pulse detected by a detector that detects light from fluorescent reference particles that emit fluorescence having a predetermined wavelength bandwidth and the control signal of the detector at the time of detecting the feature amount of the output pulse, the feature amount of the output pulse being dependent on the control signal of the detector.

The feature amount of the output pulse may be a height of the output pulse or an area of the output pulse. In particular, the feature amount of the output pulse may be a height of the output pulse.

The information processing step may correct the control signal on the basis of the applied voltage coefficient.

In the present technology, the "fine particles" widely include cells, microorganisms, bio-related fine particles such as liposome, latex particles, gel particles, synthetic particles such as industrial particles, and the like.

The bio-related fine particles include chromosome, liposomes, mitochondrias, and organelles that form a variety of cells. The cells include animal cells (for example, erythroid cells or the like) and vegetable cells. The microorganisms include bacteria such as *E. coli*, viruses such as tobacco mosaic virus, fungi such as yeast cells, and the like. Furthermore, the bio-related fine particles may include bio-related polymers such as nucleic acids, proteins, and composites thereof. Also, the industrial particles may be, for example, organic or inorganic polymer materials, metals, and the like. The organic polymer materials include polystyrene, styrene-divinylbenzene, polymethyl methacrylate, and the like. The inorganic polymer materials include glass, silica, magnetic materials, and the like. The metals include gold colloid, aluminum, and the like. The shape of the fine particles is generally spherical. According to the present technology, it may be non-spherical and the size, the weight, and the like may not be especially limited.

Advantageous Effects of Invention

According to the present technology, an output level difference can be corrected with high accuracy in fine particle measurement that optically measures properties of fine particles. It should be noted that the effects described here are not necessarily limitative and may be any of effects described in the present disclosure.

MODE(S) FOR CARRYING OUT THE INVENTION

Hereinafter, preferable embodiments of the present technology will be described with reference to the drawings. The embodiments described below illustrate typical embodiments of the present technology and are not limit the scope of the present technology. Note that the embodiments of the present technology will be described in the following order.
1. Fine particle measurement apparatus 1
(1) Detector 11
(2) Information processor 12
[Method of standardizing sensitivity of PMTs among apparatuses]
[Accuracy improvement measure]
[Method of standardizing sensitivity of a plurality of PMTs]
(3) Light irradiator 13
(4) Dispenser 14
(5) Memory 15
(6) Flow path P
(7) Display 16
(8) User interface 17
2. Information processing apparatus 10
(1) Information processor 12
(2) Memory 15
(3) Others
3. Information processing method
<1. Fine Particle Measurement Apparatus 1>

Figure 1:
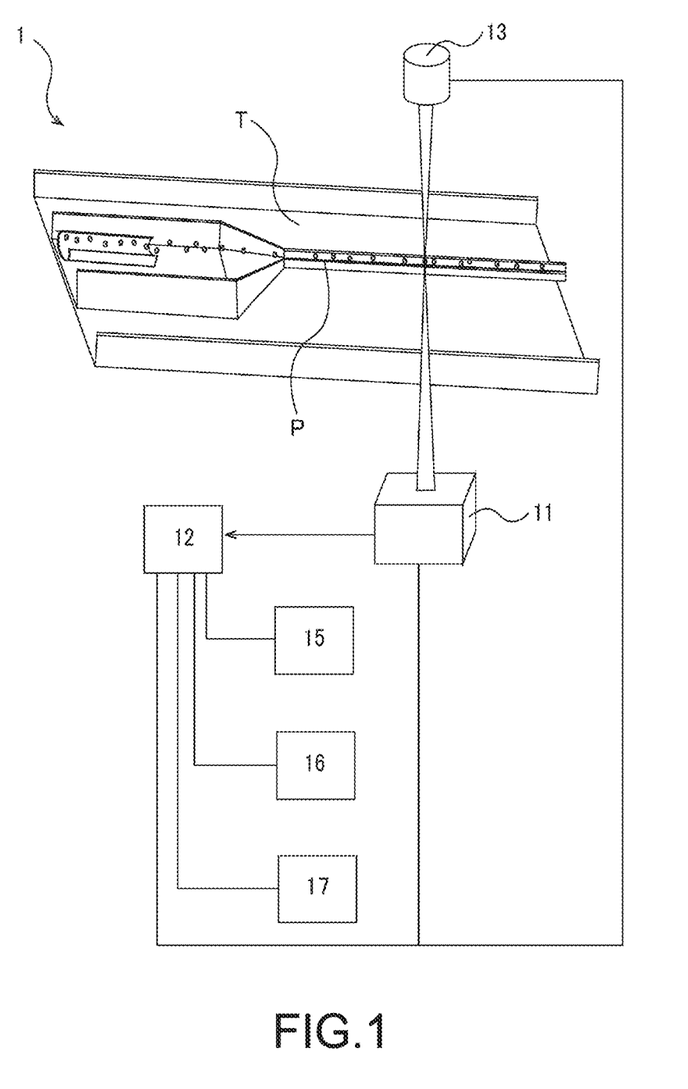
FIG. 1 is a schematic diagram schematically showing a first embodiment of a fine particle measurement apparatus 1 according to the present technology.
Figure 2:
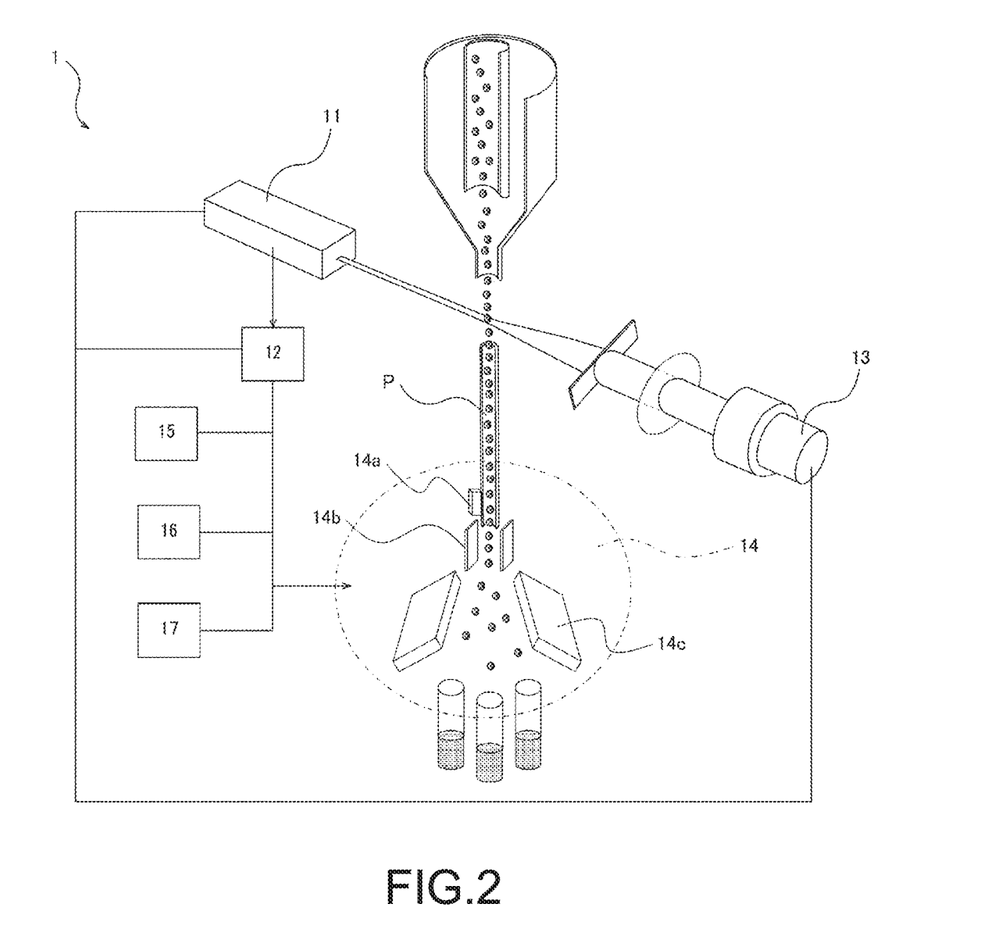
FIG. 2 is a schematic diagram schematically showing a second embodiment of the fine particle measurement apparatus 1 according to the present technology.

FIG. 1 is a schematic diagram schematically showing a first embodiment of a fine particle measurement apparatus 1 according to the present technology, and FIG. 2 is a schematic diagram schematically showing a second embodiment of the fine particle measurement apparatus 1 according to the present technology. The fine particle measurement apparatus 1 according to the present technology is an apparatus of optically measuring properties of fine particles and includes at least a detector 11 and an information processor 12. Also, the fine particle measurement apparatus 1 may include a light irradiator 13, a dispenser 14, a memory 15, a flow path P, a display 16, a user interface 17, and the like, as necessary. Hereinafter, each unit will be described in detail.

(1) Detector 11

The detector 11 detects light from fluorescent reference particles that emit fluorescence having a predetermined wavelength bandwidth and also can detect light from fine particles. The type of the detector 11 that can be used in the present technology is not especially limited as long as light from fluorescent reference particles can be detected. Any known light detectors can be freely selected and used. For example, one, two, or more of a fluorometry device, a scattered light measurement device, a transmitted light measurement device, a reflected light measurement device, a diffracted light measurement device, a ultraviolet spectrometer, an infrared spectrometer, a Raman spectrometer, a FRET measurement device, a FISH measurement device, other various spectrum measurement devices, a so-called multi-channel light detector in which a plurality of light detectors are arranged in an array, and the like can be used freely in combination.

According to the present technology, the detector 11 may be an area image sensor such as a CCD and a CMOS, a PMT, a photodiode, or the like. Among them, the detector 11 is preferably the PMT. By using the present technology, especially in a case that the detector 11 is the PMT, an output level difference can be corrected with high accuracy.

According to the present technology, the detector 11 preferably includes a plurality of light-receiving devices having different detection wavelength regions. Since the detector 11 includes a plurality of light-receiving devices having different detection wavelength regions, light intensity within the continuous wavelength region can be measured as a fluorescence spectrum. Specific examples include a PMT array or a photodiode array in which light-receiving devices are one-dimensionally arranged and those including a plurality of independent detection channels such as two-dimensional light-receiving devices, e.g., CCD, CMOS, or the like. Among them, the detector 11 preferably includes a plurality of PMTs.

In a case where the detector 11 includes the plurality of PMTs, there may be an output difference among the plurality of PMTs, as shown in [method of standardizing sensitivity of a plurality of PMTs] described later. In this manner, the output of each PMT can be set at a desirable level in one device and user's convenience upon the measurement will be thus enhanced.

The location of the detector 11 of the fine particle measurement apparatus 1 is not especially limited as long as light from the fluorescent reference particles can be detected, and can be freely designed. For example, as shown in FIGS. 1 and 2, the detector 11 is preferably located at a side opposite to the light irradiator 13 across the flow path P, as described later. By locating the detector 11 at a side opposite to the light irradiator 13 across the flow path P, the detector 11 and the light irradiator 13 can be located in a more free arrangement. In addition, as fluorescence is also emitted in a direction different from an incident direction of irradiated light, for example, the detector 11 may be located at the same side of the light irradiator 13 or at the side at an angle of 90 degrees of the light irradiator 13 relative to the flow path P.

(2) Information Processor 12

The information processor 12 performs information processing and control of the detector 11, the light irradiator 13, the dispenser 14, the memory 15, the display 16, the user interface 17, and the like. As the information processing, a relationship between an applied voltage coefficient corresponding to a feature amount of a predetermined output pulse and a control signal of the detector 11 is specified on the basis of a feature amount of an output pulse detected by the detector 11 and the control signal of the detector 11 at the time of detecting the feature amount of the output pulse. According to the present technology, the feature amount is dependent on the control signal of the detector 11.

According to the present technology, by using the above-described structure of the information processor 12, the control signal of the detector 11 is standardized. So a variation in sensitivities such as anode sensitivities (outputs from the detector such as the PMT set at a predetermined voltage) can be eliminated among the devices or within the devices over time. Thus, even if an absolute output of the device is changed due to a difference for each detector or over time, it is possible to measure at the same output level.

In addition, it is possible to provide data compatibility among the apparatuses or within the apparatus. Thus, it is unnecessary to correct data inconsistency caused by the variation in sensitivities of the detector and user's convenience will be enhanced at the time of using the data.

The feature amount of the output pulse is not especially limited as long as the value is dependent on the control signal of the detector 11. According to the present technology, the feature amount of the output pulse is preferably a height of the output pulse or an area of the output pulse, more preferably the height of the output pulse. This allows the output level difference to be corrected with higher accuracy.

In addition, according to the present technology, a median or mean value of the values can be used. It is preferable to use the median value such as a Height Median (median value of height of output pulse) and an Area Median (mean value of area of output pulse).

The fluorescent reference particles that can be used in the present technology are particles that emit fluorescence having a predetermined wavelength bandwidth. The fluorescent reference particles can be freely selected from particles that emit fluorescence having a predetermined wavelength bandwidth depending on the types of the fine particle measurement apparatus 1 and the detector 11, the types of the fine particles to be measured, measurement purposes, and the like.

Specific examples of the fluorescent reference particles include, align check beads, Ultra Rainbow fluorescent particles, and the like, for example. The condition that the particles can be used as the fluorescent reference particles is that sufficient fluorescence intensity is provided within the wavelength bandwidth of the sensitivity of the PMT to be corrected. Alternatively, it is possible to use particles such as beads labelled with fluorescent dye, for example. As the fluorescent dye that can be used in the present technology, one, two, or more of Cascade Blue, Pacific Blue, Fluorescein isothiocyanate (FITC), Phycoerythrin (PE), Propidiumiodide (PI), Texas red (TR), Peridinin chlorophyll protein (PerCP), Allophycocyanin (APC), 4',6-Diamidino-2-phenylindole (DAPI), Cy3, Cy5, Cy7, and the like can be freely used in combination, for example.

In a case where the detector 11 includes a plurality of light-receiving devices having different detection wavelengths, the wavelength bandwidth of fluorescence emitted from the fluorescent reference particles covers preferably at least a part, more preferably all of the detection wavelength regions of the respective light-receiving devices. For example, a typical flow cytometer preferably selects particles that emit fluorescence having a wavelength bandwidth of 400 to 800 nm.

The relationship between the applied voltage coefficient corresponding to a feature amount of a predetermined output pulse and a control signal of the detector 11 can be specified by using an undefined method depending on the types of the fine particle measurement apparatus 1 and the detector 11, the types of the fine particles to be measured, the measurement purposes, and the like. For example, the applied voltage coefficient can be calculated on the basis of an HV (High Voltage) and the Height Median (median value of height of output pulse) obtained from the fluorescent reference particles. Hereinafter, an illustrative specific method of specifying the applied voltage coefficient will be described.

[Method of Standardizing Sensitivity of PMTs Among Apparatuses]

"Specifying Relationship Between Applied Voltage Coefficient and HV Value for Sensitivity Standardization"

Figure 3:
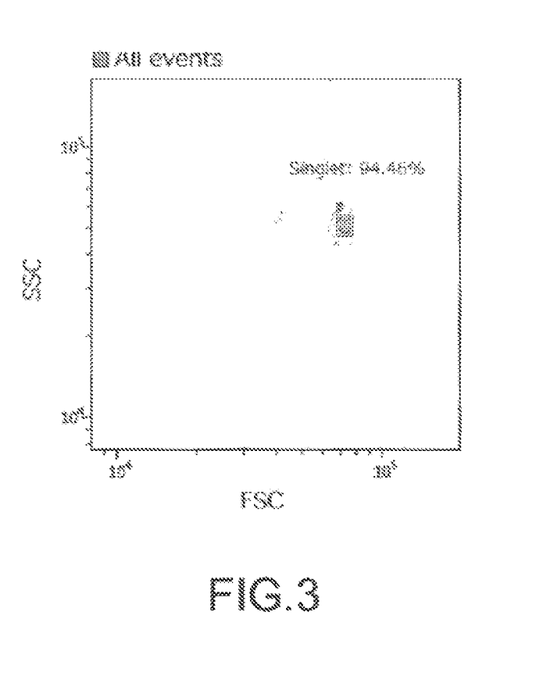
FIG. 3 is a diagram showing that only a Singlet (data where only one particle flows) is gated in a two-dimensional plot of Forward Scatter/Side Scatter ("FSC/SSC").

(a) In a two-dimensional plot of Forward Scatter/Side Scatter (hereinafter referred to as "FSC/SSC") provided by adjusting the PMT to an HV initial value and measuring the fluorescent reference particles, a Singlet (data where only one particle flows) part is gated, as shown in FIG. 3.

(b) In a narrow group gated, a median value (Median) (hereinafter referred to as "Height Median") is calculated from the height of the output pulse (Height) of the PMT.

(c) The HV is adjusted until the Height Median has a predetermined numerical range (for example, adjustment range of Height Median=60,000±10%) to specify the corresponding HV.

(d) The above-described (a) to (c) processing is performed in a different numerical range of the Height Median to specify the corresponding HV. Note that the above-described (a) to (c) processing is performed in a plurality of numerical ranges so that it can be approximated to a linear function.

Specifically, the HVs are acquired in the numerical ranges at four points (adjustment range of Height Median=600, 6000, 60000, 600000±10%), for example HV.

Figure 4:
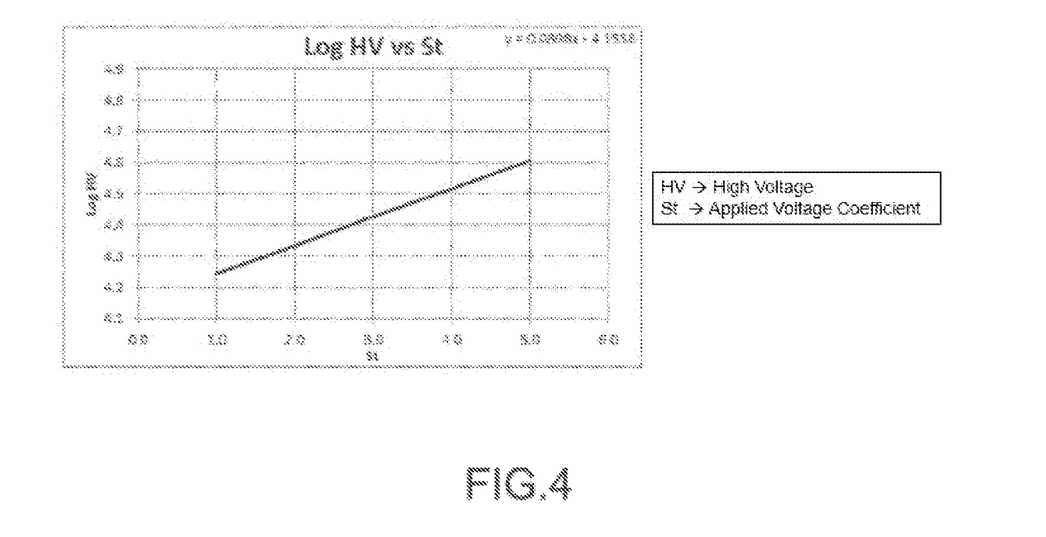
FIG. 4 is a graph substituting a drawing showing a linear relationship where a vertical axis is Log High Voltage (HV) and a horizontal axis is applied voltage coefficient (St) in a PMT (X).
Figure 5:
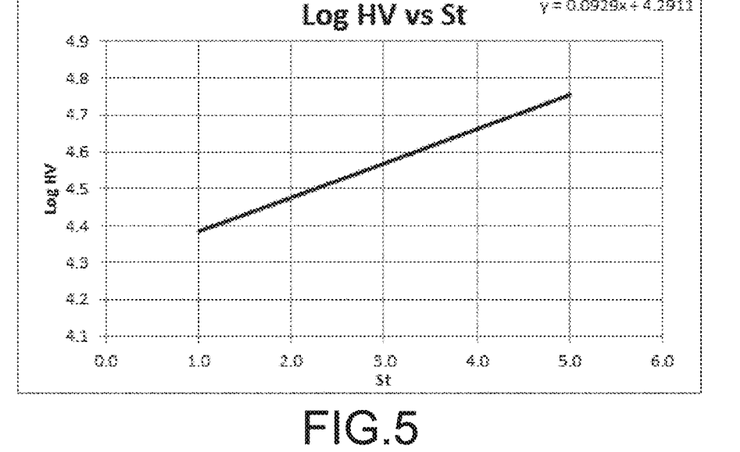
FIG. 5 is a graph substituting a drawing showing a linear relationship where a vertical axis is Log HV and a horizontal axis is St in a PMT (Y).

(e) From correspondence between the acquired Height Medians and the HVs, Log HV and Log Height Median are plotted as axes, as shown in FIGS. 4 and 5, to determine the linear function. At this time, the Log Height Median is defined as the applied voltage coefficient "St". Then, the St is assigned to x and the Log HV is assigned to y to determine a and b of y=ax+b.

Specifically, when the Height Median is 10,000 (Log Height Median is 4), the St is defined to 3, for example. Further, in a case where the Height Median is increased 10 times, the St is set to be increased by 1.0. Where the St is assigned to x and the Log HV is assigned to y, a=0.0898, b=4.1556 of PMT_1 as shown in FIG. 4 and a=0.0929, b=4.2911 of PMT_2 having the sensitivity lower than that of the PMT_1 as shown in FIG. 5.

An illustrative detailed method of determining a and b is of using the following mathematical expressions (1) to (5), for example.

First, an HV1 initial value is set on the basis of the HV value when Height Median=60,000 specified in the former measurement. The HV is adjusted so that the Height Median is included in the numerical range as described above. Then, the HV1 and the Height Median1 are acquired.

Next, a1 (for example, predetermined value specified at the former measurement) is used, an HV2 initial value of an adjustment target value (hereinafter referred to as "Target") 2 of the Height on the basis of the following mathematical expression (1), and the adjustment of the HV is started therefrom. Then, the HV2 and the Height Median2 are acquired.

[Math. 1]

$$HV2 \text{ initial value} = HV1 * \left(\frac{\text{Target2}}{\text{Height Median1}}\right)^{a1} \quad (1)$$

On the basis of the following mathematical expressions (2) and (3), an HV3, a Height Median3, an HV4, and a Height Median4 are acquired similarly.

[Math. 2]

$$HV3 \text{ initial value} = HV1 * \left(\frac{\text{Target3}}{\text{Height Median1}}\right)^{a1} \quad (2)$$

[Math. 3]

$$HV4 \text{ initial value} = HV1 * \left(\frac{\text{Target4}}{\text{Height Median1}}\right)^{a1} \quad (3)$$

From the Height Medians (Height Median1 to 4) at four points, St1 to 4 are determined using the following mathematical expression (4). Note that in the mathematical expression (4), Hst3 is a Height Median value where St is a value of 3.0.

[Math. 4]

$$St = \text{Log}\left(\frac{\text{Height Median}}{Hst3}\right) + 3 \quad (4)$$

From St1 to 4 and HV1 to 4 determined as described above, a and b are further determined by using the following mathematical expression (5).

[Math. 5]

$$\text{Log}(HV) = a*St + b \quad (5)$$

Note that the mathematical expression is based on the following fundamental equation.

[Math. 6]

$$(St2 - St1) = \text{Log}\left(\frac{\text{Height Median2}}{Hst3}\right) - \text{Log}\left(\frac{\text{Height Median1}}{Hst3}\right) =$$
$$\text{Log}\left(\frac{\text{Height Median2}}{\text{Height Median1}}\right)$$
$$\text{Log}(HV2) - \text{Log}(HV1) = \text{Log}\left(\frac{HV2}{HV1}\right) =$$
$$a*(St2 - St1) = \text{Log}\left(\frac{\text{Height Median2}}{\text{Height Median1}}\right)^a$$
$$HV2 = HV1 * \left(\frac{\text{Height Median2}}{\text{Height Median1}}\right)^a$$

"Setting of HV Value Upon Measurement Using Applied Voltage Coefficient"

Upon the measurement, a corresponding HV value is set using correspondence between the ST and the HV recorded on the basis of the applied voltage coefficient St. Specifically, the HV can be determined in light of the linear function recorded on the basis of the St value set by the user, for example. In this manner, in a case where the PMT_1 and the PMT_2 have different sensitivities, the HV can be set so that experimental results can be similarly provided, as below.

TABLE 1

| Height Median of align check beads | Applied voltage coefficient (St) | PMT (X) Log HV | PMT (Y) Log HV |
|---|---|---|---|
| 100 | 1.0 | 4.25 | 4.38 |
| 1,000 | 2.0 | 4.34 | 4.48 |
| 10,000 | 3.0 | 4.43 | 4.57 |
| 100,000 | 4.0 | 4.51 | 4.66 |
| 1,000,000 | 5.0 | 4.60 | 4.76 |

[Accuracy Improvement Measure]

Figure 6:
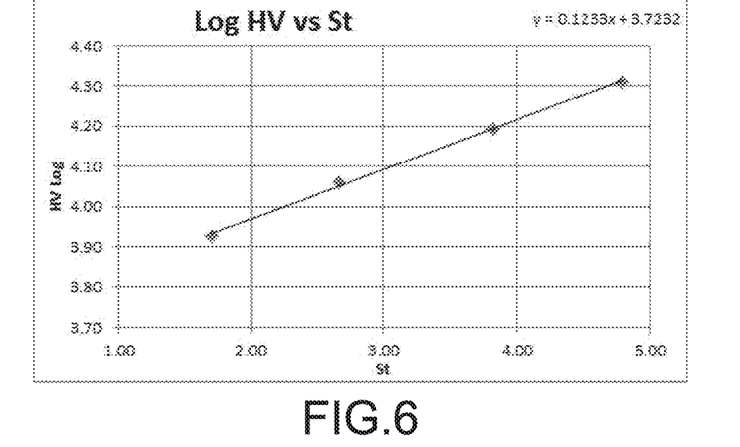
FIG. 6 is a graph substituting a drawing showing a relationship where a linear function is applied (vertical axis: Log HV, horizontal axis: St) in a method of standardizing sensitivity.
Figure 7:
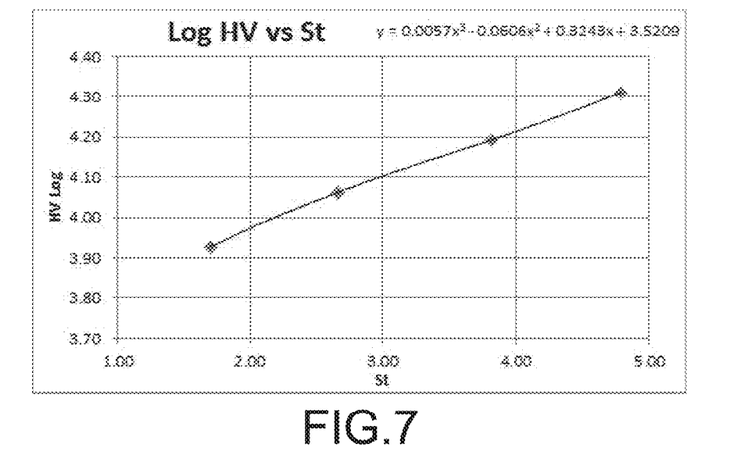
FIG. 7 is a graph substituting a drawing showing a relationship where a cubic function is applied (vertical axis: Log HV, horizontal axis: St) in a method of standardizing sensitivity.

In the former description, an approximation by the linear function is applied to the relationship between the applied voltage coefficient and the Log HV. Further accuracy improvement can be achieved by increasing the degree of the approximation. In fact, the applied voltage coefficient and the Log HV may slightly deviate from the linear characteristic due to a setting range of the HV and characteristics of the PMT itself. At this time, there is an error when the linear function is applied, but the accuracy is improved when a cubic function is applied. Specifically, where the linear function is applied, the second point from left deviates from the linearity as shown in FIG. 6, for example, and the accuracy around the second point is decreased. On the other hand, where the cubic function is applied as shown in FIG. 7, the four points are on the approximation curve, which shows that the accuracy is improved.

[Method of Standardizing Sensitivity of a Plurality of PMTs]

"Specifying Relationship Between Applied Voltage Coefficient and HV Value for Sensitivity Standardization"

In a case where one flow cytometer includes a plurality of PMTs, it is possible to control HVs of the plurality of PMTs by one HV with a ratio of sensitivities being set to a fixed value and the respective PMTs in the apparatus being standardized.

(a) For example, it considers that one flow cytometer includes four PMTs (PMT_A to PMT_D). An output ratio of the PMT_A:PMT_B:PMT_C:PMT_D is set to 1:2:3:4 where align check beads are used and an adjustment target is that the Height Median value of the PMT_A is 10,000 where the St is 3.0. At this time, the following procedures are considered.

(b) By referring to the above-described (a) to (d) of [Method of standardizing sensitivity of PMTs among apparatuses], the Height Medians and the HV data of each PMT are acquired at four points.

(c) From correspondence between the acquired Height Medians and the HVs, Log HV and Log Height Median are plotted as axes to determine the linear function. At this time, the Log Height Median is defined as the applied voltage coefficient "St". Then, the St is assigned to x and the Log HV is assigned to y to determine a and b of y=ax+b where the above-described adjustment target (PMT_A:PMT_B:PMT_C:PMT_D=1:2:3:4 and the Height Median value of the PMT_A is 10,000 where the St is 3.0) is satisfied.

"Setting of HV Value Upon Measurement Using Applied Voltage Coefficient"

Upon the measurement, a corresponding HV value is set using correspondence between the ST and the HV recorded on the basis of the applied voltage coefficient St. Specifically, the HV can be determined in light of the linear function recorded on the bases of the St value set by the user, for example. In this manner, in a case where the respective PMTs in the apparatus have different sensitivities, one HV can control the HVs of the plurality of PMTs.

Note that the applied voltage coefficient (St) is calculated by using the Height Median in the two specific embodiments. Alternatively, according to the present technology, it is possible to use the Area Median (mean value of area of output pulse) in place of the Height Median. In addition, the applied voltage coefficient is not especially limited and can be calculated by any setting as long as it corresponds to a predetermined feature amount of the output pulse. Furthermore, in the two specific embodiments, the line is determined by plotting in four points, but it is not limited thereto and plotting may be at two points or more according to the present technology.

In addition, according to the present technology, the correspondence between the St and the HV is stored upon measurement by determining not only a primary straight line but also a correspondence table. Furthermore, the St value is set upon measurement not only by the user but also by the information processor 12 on the basis of samples to be measured, conditions, and the like.

(3) Light Irradiator 13

The fine particle measurement apparatus 1 according to the present technology may further include a light irradiator 13 that irradiates fluorescent reference particles or fine particles with light. The type of light irradiated from the light irradiator 13 is not especially limited. In order to reliably generate fluorescence or scattered light from particles, the light having fixed light direction, wavelength, and light intensity is preferable. Specific examples include a laser, an LED, and the like. In a case where laser is used, the type is not especially limited and one, two, or more of an argon ion (Ar) laser, a helium-neon (He—Ne) laser, a dye laser, a krypton (Cr) laser, semiconductor laser, or a solid-state laser by combining a wavelength conversion optical element with a semiconductor laser can be freely used in combination.

(4) Dispenser 14

The fine particle measurement apparatus 1 according to the present technology further include a dispenser 14 that dispenses fine particles. For example, the dispenser 14 dispenses fine particles on the basis of spectral data generated by correcting the value, which is detected by the detector 11, by the information processor 12. The dispenser 14 can dispense fine particles at downstream of the flow path P on the basis of analysis results of sizes, morphology, internal structures of the fine particles analyzed from the spectral data.

Specifically, liquid droplets are generated from a discharge port or the like of the flow path P by oscillating the whole or a part of the flow path P using an oscillator 14a or the like that oscillates at the predetermined number of oscillation, for example, as shown in FIG. 2. Note that, in this case, the oscillator 14a used is not especially limited and any known oscillators can be freely selected and used. Examples include a piezo oscillator and the like. In addition, by adjusting a liquid amount fed to the flow path P, the diameter of the discharge port, the number of oscillation of the oscillator, and the like, the size of the liquid droplets is adjusted to generate the liquid droplets including a fixed amount of the fine particles.

Next, plus or minus electric charges are charged on the basis of the analysis results of sizes, morphology, internal structures of the fine particles analyzed from the spectral data generated by the correction by the information processor 12 (see sign 14b of FIG. 2). Then, a counter electrode 14c to which a voltage is applied changes courses of the charged liquid droplets in a desirable direction and the fine particles therein are dispensed.

(5) Memory 15

The fine particle measurement apparatus 1 according to the present technology may further include a memory 15 that stores a relationship (for example, linear function, correspondence table, or the like) between the HV and the applied voltage coefficient. The memory 15 can also store all items about the measurement including the values detected by the detector 11, the spectral data generated by the information processor 12, a reference spectrum for each channel, the relationship between the HV and the applied voltage coefficient specified at the former measurement, and the like other than the relationship between the HV and the applied voltage coefficient.

The memory 15 is not essential in the fine particle measurement apparatus 1 and an external memory unit may be connected. As the memory 15, a hard disk or the like can be used, for example.

(6) Flow Path P

The fine particle measurement apparatus 1 according to the present technology may further include the flow path P. In the fine particle measurement apparatus 1 according to the present technology, optical information acquired from fine particles aligned in a row within a flow cell (flow path P) is detected to analyze and dispense the fine particles.

The fine particle measurement apparatus 1 may include the flow path P in advance. Alternatively, a commercially available flow path P, a disposable chip including the flow path P, or the like may be disposed on the fine particle measurement apparatus 1 for analysis or dispensing.

The geometry of the flow path P is not especially limited and may be freely designed. For example, not only the flow path P formed in a substrate T made of two-dimensional or three-dimensional plastic or glass shown in FIG. 1 but also the flow path P used in the flow cytometer in the related art shown in FIG. 2 may be used in the fine particle measurement apparatus 1 according to the present technology.

In addition, a flow path width, a flow path depth, a flow path cross-sectional shape of the flow path P are not especially limited and can be freely designed as long as a laminar flow can be formed. For example, a microflow path having a flow path width of 1 mm or less can be used in the fine particle measurement apparatus 1. In particular, the microflow path having a flow path width of from about 10 µm to about 1 mm can be suitably used in the fine particle measurement apparatus 1 according to the present technology.

(7) Display 16

The fine particle measurement apparatus 1 according to the present technology may further include a display 16. The display 16 can display all items about the measurement including the values detected by the detector 11, the spectral data generated by the information processor 12, the calculated applied voltage coefficient, the reference spectrum for each channel, and the like.

The display 16 is not essential in the fine particle measurement apparatus 1 and an external display unit may be connected. As the display 16, a display, a printer, or the like can be used, for example.

(8) User Interface 17

The fine particle measurement apparatus 1 according to the present technology may further include a user interface 17 whereby a user operates. The user can access the information processor 12 through the user interface 17 and control each unit of the fine particle measurement apparatus 1 according to the present technology.

The user interface 17 is not essential in the fine particle measurement apparatus 1 and an external operation unit may be connected. As the user interface 17, a mouse, a keyboard, or the like can be used, for example.

<2. Information Processing Apparatus 10>

Figure 8:
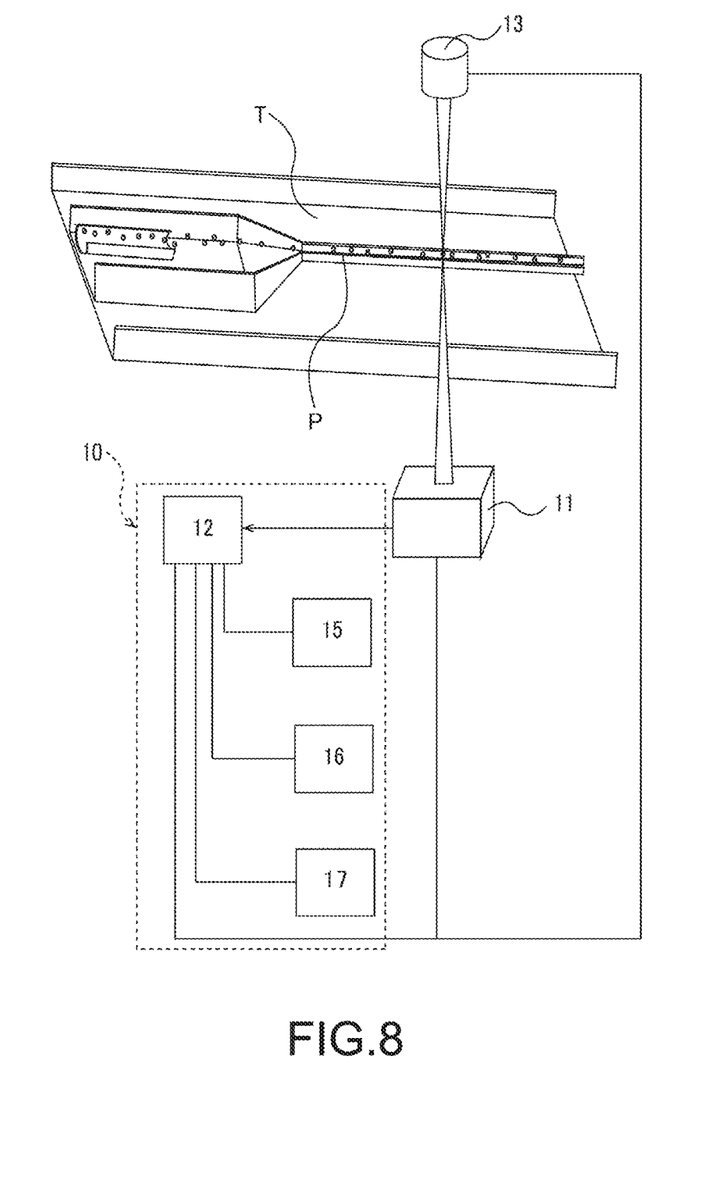
FIG. 8 is a schematic diagram schematically showing an illustrative flow cytometer in which a first embodiment of an information processing apparatus 10 according to the present technology can be used.
Figure 9:
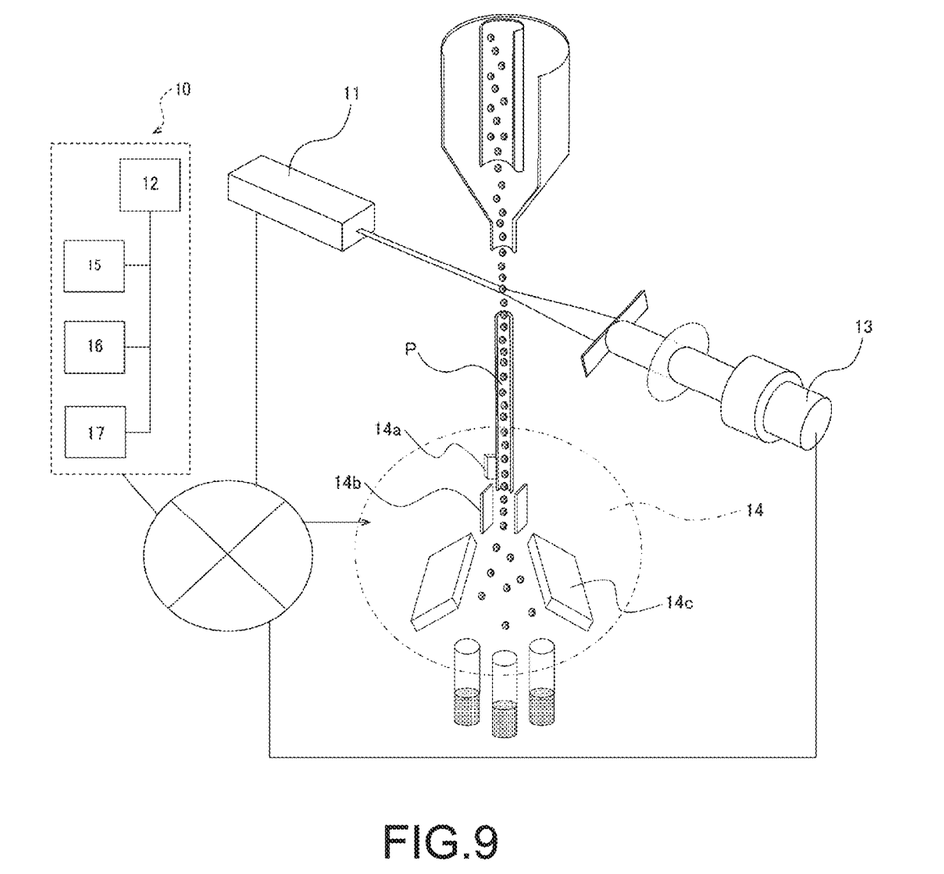
FIG. 9 is a schematic diagram schematically showing an illustrative flow cytometer in which a second embodiment of the information processing apparatus 10 according to the present technology can be used.

FIG. 8 is a schematic diagram schematically showing an illustrative flow cytometer in which a first embodiment of an information processing apparatus 10 according to the present technology can be used, and FIG. 9 is a schematic diagram schematically showing an illustrative flow cytometer in which a second embodiment of the information processing apparatus 10 according to the present technology can be used. The information processing apparatus 10 according to the present technology includes at least the information processor 12. Also, the information processing apparatus 10 may include the memory 15, the display 16, the user interface 17, and the like, as necessary. Hereinafter, each unit will be described in detail. Note that as the display 16 and the user interface 17 are the same as the display 16 and the user interface 17 of the fine particle measurement apparatus 1 described above in detail, description of which is omitted.

(1) Information Processor 12

The information processor 12 performs information processing and control of the memory 15, the display 16, the user interface 17, and the like. As the information processing, a relationship between an applied voltage coefficient corresponding to a feature amount of a predetermined output pulse and a control signal of the detector on the basis of a feature amount of an output pulse detected by a detector that detects light from fluorescent reference particles that emit fluorescence having a predetermined wavelength bandwidth and the control signal of the detector at the time of detecting the feature amount of the output pulse is specified. According to the present technology, the feature amount is dependent on the control signal of the detector.

Note that as the detail of the information processing performed by the information processor 12 and the detail of the fluorescent reference particles are the same as the information processing method performed by the information processor 12 and the fluorescent reference particles used in the fine particle measurement apparatus 1 described above, description of which is omitted.

(2) Memory 15

According to the present technology, as shown in FIGS. 8 and 9, the information processing apparatus 10 may further include the memory 15 that stores the applied voltage coefficient. Note that as the detail of the memory 15 is the same as the memory 15 of the fine particle measurement apparatus 1, description of which is omitted.

(3) Others

The information processing apparatus 10 according to the present technology may include the display 16 and the user interface 17, as shown in FIGS. 8 and 9. Also, as shown in FIG. 9, the information processing apparatus 10 can be connected to each unit of the flow cytometer (detector 11, light irradiator 13, dispenser 14, or the like) via a network. Furthermore, the memory 15, the display 16, and the user interface 17 can be provided outside the information processing apparatus 10 and connected via a network (not shown).

<3. Information Processing Method>

The information processing method according to the present technology performs at least an information processing step. The specific information processing method performed in the information processing step is the same as the information processing method performed by the information processor 12 of the information processing apparatus 10 described above. Hereinafter, an illustrative flow of fine particle measurement using the information processing method according to the present technology will be described with reference to FIGS. 10 and 11. Note that processing in each step of the flowcharts shown in FIGS. 10 and 11 is performed by the above-described detector 11, the information processor 12, or the like, for example.

Figure 10:
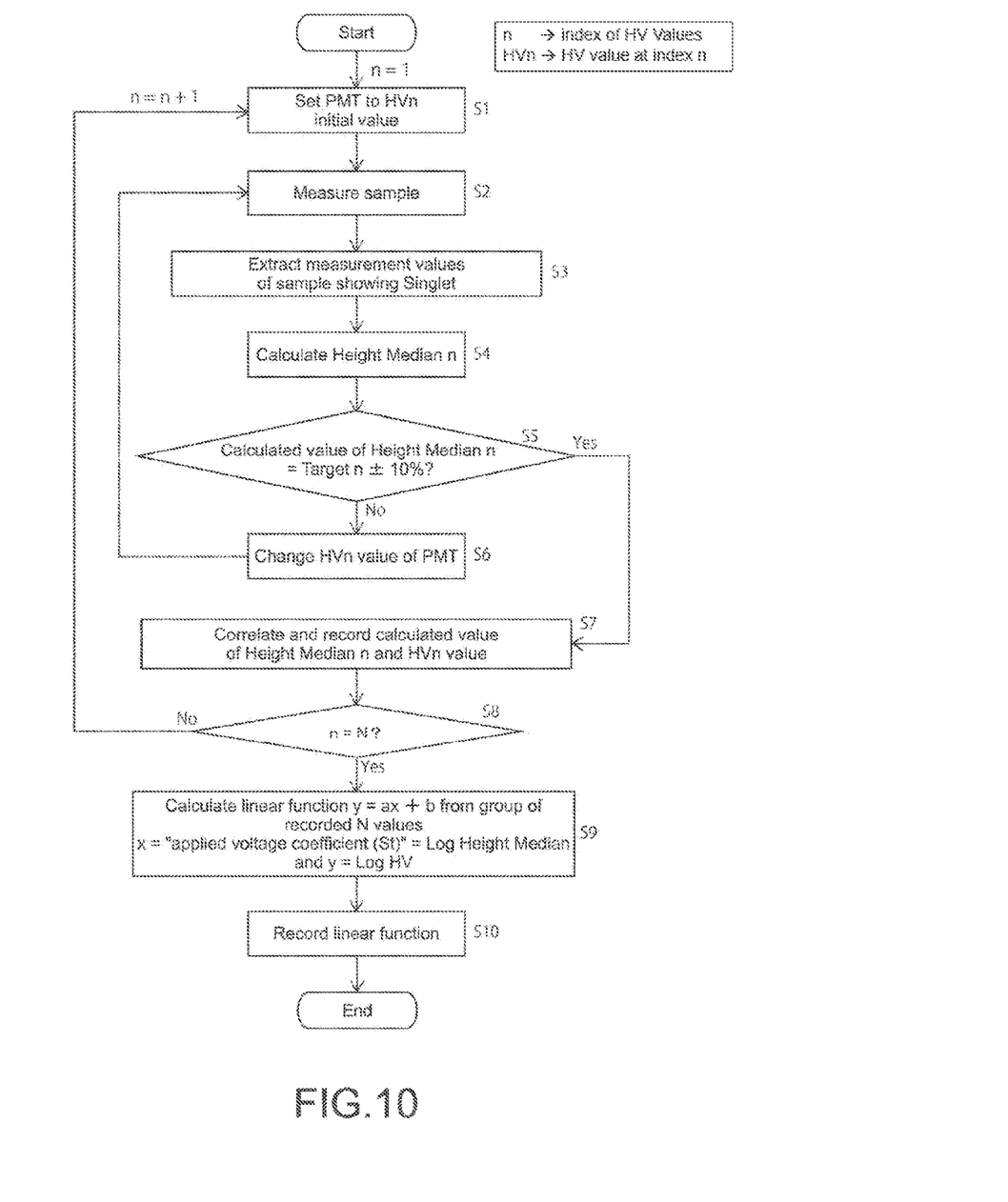
FIG. 10 is a flowchart showing an example of an information processing method according to the present technology.
Figure 11:
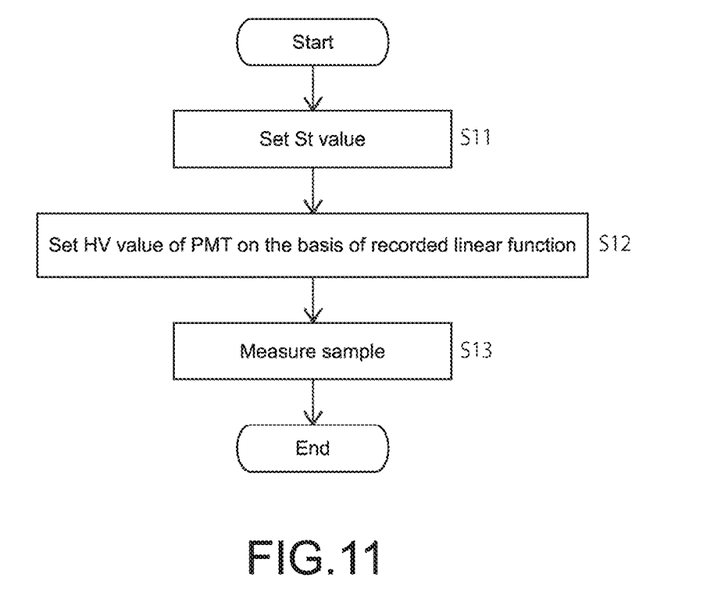
FIG. 11 is a flowchart showing illustrative measurement of fine particles using a linear function recorded by the information processing method according to the present technology.

FIG. 10 is a flowchart showing an example of the information processing method according to the present technology and shows a flow about specifying the relationship between the applied voltage coefficient (St) and the HV value for sensitivity standardization of the PMT.

First, the PMT is set to an HV1 initial value (Step S1). Next, a sample measurement is performed (Step S2) and measurement values of the sample showing Singlet are extracted (Step S3). Thereafter, Height Median1 is calculated (Step S4). Then, in Step S5, in a case where the calculated value of the Height Median1 is determined to be not a Target1±10%, the HV1 value of the PMT is changed (Step S6) and it returns to Step S2. Steps S2 to S6 are repeated until the calculated value of the Height Median1 is included in the Target1±10%. In a case where the calculated value is determined to be the Target1±10%, the calculated value of the Height Median1 and the HV1 value are correlated and recorded (Step S7).

After the calculated value of the Height Median1 and the HV1 value are recorded, the PMT is set to an HV2 initial value (Step S1). Steps S2 to S6 are repeated until the calculated value of the Height Median2 reaches the Target2±10%. Similarly, the calculated value of the Height Median2 and the HV2 value are recorded (Step S7). The above-described processing is performed in a numerical range of N Heights enough to be approximated to a linear function and the calculated values of N Height Medians and the HV value are recorded (Step S8). The linear function $y=ax+b$ is calculated from a group of recorded N values. At this time, x="applied voltage coefficient (St)"=Log Height Median and y=Log HV (Step S9). Then, the linear function is recorded (Step S10) and the processing is ended.

FIG. 11 is a flowchart showing illustrative measurement of fine particles using the linear function recorded by the information processing method according to the present technology and shows a flow about the sample measurement based on a setting of the applied voltage coefficient (St).

First, the St value is set (Step S11). Next, on the basis of the recorded linear function, the HV value of the PMT is set (Step S12). Thereafter, the sample measurement is performed (Step S13) and the processing is ended.

Note that the present technology may also have the following structures.

(1) A fine particle measurement apparatus, including:

a detector that detects light from fluorescent reference particles that emit fluorescence having a predetermined wavelength bandwidth; and an information processor that specifies a relationship between an applied voltage coefficient corresponding to a feature amount of a predetermined output pulse and a control signal of the detector on the basis of a feature amount of an output pulse detected by the detector and the control signal of the detector at the time of detecting the feature amount of the output pulse, the feature amount of the output pulse being dependent on the control signal of the detector.

(2) The fine particle measurement apparatus according to (1), in which
the detector includes a plurality of PMTs.
(3) The fine particle measurement apparatus according to (2), in which
there is an output difference among the plurality of PMTs.
(4) The fine particle measurement apparatus according to any one of (1) to (3), in which
the feature amount of the output pulse is a height of the output pulse or an area of the output pulse.
(5) The fine particle measurement apparatus according to according to any one of (1) to (4), in which
the feature amount of the output pulse is a height of the output pulse.
(6) The fine particle measurement apparatus according to any one of (1) to (5), in which
the information processor corrects the control signal on the basis of the applied voltage coefficient.
(7) The fine particle measurement apparatus according to (6), in which
the detector to which the corrected control signal is input measures target fine particles.
(8) An information processing apparatus, including:
an information processor that specifies a relationship between an applied voltage coefficient corresponding to a feature amount of a predetermined output pulse and a control signal of the detector on the basis of a feature amount of an output pulse detected by a detector that detects light from fluorescent reference particles that emit fluorescence having a predetermined wavelength bandwidth and the control signal of the detector at the time of detecting the feature amount of the output pulse,
the feature amount of the output pulse being dependent on the control signal of the detector.
(9) The information processing apparatus according to (8), in which
the feature amount of the output pulse is a height of the output pulse or an area of the output pulse.
(10) The information processing apparatus according to (8) or (9), in which
the feature amount of the output pulse is a height of the output pulse.
(11) The information processing apparatus according to any one of (8) to (10), in which
the information processor corrects the control signal on the basis of the applied voltage coefficient.
(12) The information processing apparatus according to according to any one of (8) to (11), further including:
a memory that stores the applied voltage coefficient.
(13) An information processing method, including an information processing step of specifying a relationship between an applied voltage coefficient corresponding to a feature amount of a predetermined output pulse and a control signal of the detector on the basis of a feature amount of an output pulse detected by a detector that detects light from fluorescent reference particles that emit fluorescence having a predetermined wavelength bandwidth and the control signal of the detector at the time of detecting the feature amount of the output pulse,
the feature amount of the output pulse being dependent on the control signal of the detector.
(14) The information processing method according to (13), in which
the feature amount of the output pulse is a height of the output pulse or an area of the output pulse.
(15) The information processing method according to (13) or (14), in which
the feature amount of the output pulse is a height of the output pulse.
(16) The information processing method according to according to any one of (13) to (15), in which
the information processing step corrects the control signal on the basis of the applied voltage coefficient.
(17) The calculated values of N Height Medians and the HV value are recorded (Step S8), and the cubic function $y=ax^3+bx^2+cx+d$ is calculated from the recorded N value group and the HV value of the PMT is set (Step S12).

REFERENCE SIGNS LIST 1 fine particle measurement apparatus
11 detector
12 information processor
13 light irradiator
14 dispenser
15 memory
P flow path
T substrate
16 display
17 user interface
10 information processing apparatus

The invention claimed is:

1. A measurement apparatus, comprising:
a detector configured to:
detect light from a plurality of fluorescent reference particles, wherein the plurality of fluorescent reference particles emits fluorescence of a specific wavelength bandwidth; and
determine a height median of a first output pulse based on the detection of the light, wherein the height median of the first output pulse is a median value of a height of the first output pulse; and
an information processor configured to:
determine a relationship between an applied voltage coefficient of the detector and a control signal of the detector, wherein
the relationship is determined based on:
the height median of the first output pulse, and
the control signal of the detector at a time of the detection of the height median of the first output pulse,
the applied voltage coefficient is based on a height median of a second output pulse of the detector,
the height median of the second output pulse is a median value of a height of the second output pulse, and
the height median of the first output pulse is based on the control signal of the detector;
control the detector based on the determined relationship;
control analysis of a size of at least one fluorescent particle of the plurality of fluorescent particles based on the control of the detector; and
control a dispenser to dispense the plurality of fluorescent particles based on the analysis of the size.

2. The measurement apparatus according to claim 1, wherein the detector includes a plurality of Photo Multiplier Tubes (PMTs).

3. The measurement apparatus according to claim 2, wherein an output of a first PMT of the plurality of PMTs is different from an output of a second PMT of the plurality of PMTs.

4. The measurement apparatus according to claim 1, wherein the information processor is further configured to correct the control signal based on the applied voltage coefficient.

5. The measurement apparatus according to claim 4, wherein the detector is further configured to:
receive the corrected control signal; and
measure a plurality of target particles based on the received corrected control signal.

6. An information processing apparatus, comprising:
an information processor configured to:
determine a relationship between an applied voltage coefficient of a detector and a control signal of the detector, wherein
the relationship is determined based on:
a height median of a first output pulse detected by the detector, wherein the height median of the first output pulse is a median value of a height of the first output pulse, and
the control signal of the detector at a time of the detection of the height median of the first output pulse by the detector,
the detector detects light from a plurality of fluorescent reference particles,
the plurality of fluorescent reference particles emits fluorescence of a specific wavelength bandwidth,
the applied voltage coefficient is based on a height median of a second output pulse of the detector,
the height median of the second output pulse is a median value of a height of the second output pulse, and
the height median of the first output pulse is based on the control signal of the detector;
control the detector based on the determined relationship;
control analysis of a size of at least one fluorescent particle of the plurality of fluorescent particles based on the control of the detector; and
control a dispenser to dispense the plurality of fluorescent particles based on the analysis of the size.

7. The information processing apparatus according to claim 6, wherein the information processor is further configured to correct the control signal based on the applied voltage coefficient.

8. The information processing apparatus according to claim 6, further comprising a memory configured to store the applied voltage coefficient.

9. An information processing method, comprising:
determining a relationship between an applied voltage coefficient of a detector and a control signal of the detector, wherein
the relationship is determined based on:
a height median of a first output pulse detected by the detector, wherein the height median of the first output pulse is a median value of a height of the first output pulse, and
the control signal of the detector at a time of the detection of the height median of the first output pulse by the detector,
the detector detects light from a plurality of fluorescent reference particles,
the plurality of fluorescent reference particles emits fluorescence of a specific wavelength bandwidth,
the applied voltage coefficient is based on a height median of a second output pulse of the detector,
the height median of the second output pulse is a median value of a height of the second output pulse, and
the height median of the first output pulse is based on the control signal of the detector;
controlling the detector based on the determined relationship;
controlling analysis of a size of at least one fluorescent particle of the plurality of fluorescent particles based on the control of the detector; and
controlling a dispenser to dispense the plurality of fluorescent particles based on the analysis of the size.

10. The information processing method according to claim 9, further comprising correcting the control signal based on the applied voltage coefficient.

* * * * *